United States Patent
Peyer

(10) Patent No.: US 11,460,422 B2
(45) Date of Patent: Oct. 4, 2022

(54) METHOD FOR ON-SITE MONITORING OF THE QUALITY OF THE GASES DELIVERED TO AN INDUSTRIAL CONSUMER SITE USING THE THERMAL CONDUCTIVITY TECHNIQUE

(71) Applicants: L'Air Liquide, Societe Anonyme pour l'Etude et l'Exploitation des Procedes Georges Claude, Paris (FR); CARBAGAS, Gümligen (CH)

(72) Inventor: Heinz Peyer, Gumligen (CH)

(73) Assignees: L'Air Liquide, Societe Anonyme Pour L'Etude Et L'Exploitation Des Procedes Georges Claude, Paris (FR); CARBAGAS, Gumligen (CH)

(*) Notice: Subject to any disclaimer, the term of this patent is extended or adjusted under 35 U.S.C. 154(b) by 822 days.

(21) Appl. No.: 16/336,719

(22) PCT Filed: Jan. 30, 2019

(86) PCT No.: PCT/EP2019/052286
§ 371 (c)(1),
(2) Date: Mar. 26, 2019

(87) PCT Pub. No.: WO2019/154697
PCT Pub. Date: Aug. 15, 2019

(65) Prior Publication Data
US 2021/0364457 A1 Nov. 25, 2021

(30) Foreign Application Priority Data
Feb. 6, 2018 (EP) ..................... 18305119

(51) Int. Cl.
*G01N 25/18* (2006.01)
*G06Q 10/08* (2012.01)
*G06Q 30/00* (2012.01)
*G01N 33/00* (2006.01)

(52) U.S. Cl.
CPC ........... *G01N 25/18* (2013.01); *G06Q 10/083* (2013.01); *G06Q 30/0185* (2013.01); *G01N 33/0006* (2013.01)

(58) Field of Classification Search
CPC .... G01N 25/18; G01N 27/18; G01N 33/0006; G01N 33/0008
See application file for complete search history.

(56) References Cited

U.S. PATENT DOCUMENTS

| | | | |
|---|---|---|---|
| 5,297,419 A * | 3/1994 | Richardson | G01N 27/18 422/90 |
| 6,266,995 B1 | 7/2001 | Scott | |
| 10,935,507 B2 * | 3/2021 | Ludwig | G01N 25/18 |
| 2010/0042333 A1 * | 2/2010 | Scheffler | G01N 33/004 702/182 |
| 2012/0191349 A1 | 7/2012 | Lenz et al. | |
| 2017/0016840 A1 * | 1/2017 | Bourlon | G01N 33/0031 |
| 2018/0052124 A1 * | 2/2018 | Rogers | G01N 25/18 |
| 2019/0339188 A1 * | 11/2019 | Pejcinovic | G01N 15/0893 |

FOREIGN PATENT DOCUMENTS

| | | |
|---|---|---|
| WO | WO 2007/036983 | 4/2007 |
| WO | WO 2014/142829 | 9/2014 |

OTHER PUBLICATIONS

EP Search Report for EP 18305119, dated Aug. 3, 2018.

* cited by examiner

*Primary Examiner* — Alexander A Mercado
(74) *Attorney, Agent, or Firm* — Christopher J. Cronin

(57) ABSTRACT

The invention provides a method for on-site monitoring of the quality of the gases delivered to a consumer site, the monitoring being carried out during the delivery, in order to declare the delivery compliant or non-compliant with specifications, being characterized in that, during the delivery, a monitoring of the gas(es) delivered is carried out by the thermal conductivity technique.

1 Claim, No Drawings

METHOD FOR ON-SITE MONITORING OF THE QUALITY OF THE GASES DELIVERED TO AN INDUSTRIAL CONSUMER SITE USING THE THERMAL CONDUCTIVITY TECHNIQUE

CROSS-REFERENCE TO RELATED APPLICATIONS

This application is a § 371 of International PCT Application PCT/EP2019/052286, filed Jan. 30, 2019, which claims § 119(a) foreign priority to EP patent application EP 18305119, filed Feb. 6, 2018.

BACKGROUND

Field of the Invention

The present invention relates to the field of monitoring the quality (the "identity") of the industrial gases delivered to an industrial consumer site, very particularly in the food and pharmaceutical industry.

Related Art

These industries are in particular interested in the following gases: nitrogen, oxygen, $CO_2$, or else argon and nitrous oxide, alone or as mixtures.

Specifically it appears that these industries are implementing more and more regulatory requirements, where the acceptability of a gas delivery on the certificate of analysis alone provided by the gas producer is no longer sufficient (certificate that took into account tests carried out upstream in the gas producer's own laboratories). These industries now require tests of conformity, such as what gas and what content of a gas in a mixture, to be carried out at their industrial site, during the delivery (upon receipt).

These tests carried out at the industrial site in question, during the delivery, hence require a significant time, forcing the delivery truck to wait for the result of the tests, often several hours (using the conventional methods mentioned in the pharmacopoeias), before completing their delivery and going on to their next customer. This unquestionably represents a waste of time that is highly detrimental for the gas producer who is delivering, but also a cost, and a waste of time, and of labor, for the business customer.

SUMMARY OF THE INVENTION

One of the objectives of the present invention is then to provide a new method for the on-site monitoring of the quality (which may also be referred to as the "identity") of the gases delivered to an industrial consumer site.

As will be seen in greater detail in what follows, the invention proposes to carry out, at the industrial site delivered to, during the delivery, a monitoring of the gas or mixture delivered, by the thermal conductivity technique.

DETAILED DESCRIPTION OF THE INVENTION

According to one of the methods of implementation of the invention, a device is provided, during the delivery, for identifying the gas during the delivery thereof and the receipt thereof at the consumer site, which comprises:
- an analyzer of the thermal conductivity of the gases, which analyzer will have been precalibrated using each of the pure gases capable of subsequently being delivered, alone or as mixtures, during such a delivery ("calibration"); and
- a data acquisition and processing system,
- device for identifying the gas which is capable:
  - of acquiring one or more samples of the gas or mixture delivered;
  - of acquiring one or more samples of a reference gas such as nitrogen, preferred reference gas since it is commonly present at such sites;
  - of carrying out one or more measurements of the conductivity of the sample(s) of the reference gas and of carrying out the comparison of the measurements obtained with the thermal conductivity values obtained upstream during said "calibration" with this same reference gas;
  - of carrying out one or more measurements of the conductivity of the sample(s) of the gas or mixture delivered, and of carrying out the comparison of the measurements thus obtained with the thermal conductivity values obtained upstream during said "calibration"; and
  - of giving a diagnosis of "compliant delivery" or "non-compliant delivery" type authorizing or not authorizing the delivery of the gas or mixture delivered.

Hence the advantages which are linked to this technical proposition are understood compared to the current methods where samples are sent to the laboratory of the site delivered to, where it is necessary to wait for the feedback from this laboratory, etc.:
- this on-site qualification during the delivery is carried out in a few minutes (commonly in less than 5 minutes);
- each molecule is characterized by a single thermal conductivity value at a given temperature, and the available literature clearly shows that the thermal conductivities of gases such as air, $N_2$, $O_2$, Ar, $CO_2$, $N_2O$, $NH_3$, $O_2H_6$, or else $C_3H_8$ are clearly differentiable, and therefore make it possible to testify that such a gas and not such another is incontrovertibly present in the sample tested;
- no need here to have a calibration gas for each of the gases or mixtures delivered: the sole presence on-site (and it is proven) of a reference gas such as nitrogen, makes it possible to measure the thermal conductivity of the nitrogen as a reference, to confirm the fact that the apparatus is indeed operational and provides a value in accordance with the conductivity value of nitrogen within the observed temperature ranges, and that therefore the analysis of the thermal conductivity of the delivered gas(es) of interest may begin;
- no interference between gases can disrupt the result of the qualification;
- this method is very simple, automatic, and does not require any particular qualification or the intervention of any specialized laboratory;
- the cost of this monitoring is much lower compared to the methods currently used (by way of example, a single analyzer instead of five analyzers for monitoring the delivery of $N_2$, Ar, $O_2$, $CO_2$ and nitrous oxide);
- according to one of the advantageous methods of implementation of the invention, the device in question, which is preferentially "waterproof" i.e of waterproof construction, is "permanently" positioned in the delivery zone of the gas fluids of the industrial site in question.

The present invention then relates to a method for on-site monitoring of the quality of the gases delivered to an industrial consumer site, the monitoring being carried out during the delivery, in order to declare the delivery compliant or non-compliant with specifications, being characterized in that, during the delivery, a monitoring of the gas(es) delivered is carried out by the thermal conductivity technique, in the following manner:

providing, during the delivery, a device for identifying the gas during the delivery thereof and the receipt thereof at the consumer site, which comprises:
- an analyzer of the thermal conductivity of the gases, which analyzer will have been precalibrated using each of the pure gases capable of subsequently being delivered, alone or as mixtures, during such a delivery ("calibration"); and
- a data acquisition and processing system, device for identifying the gas which is capable:
- of acquiring one or more samples of the gas or mixture delivered;
- of acquiring one or more samples of a reference gas such as nitrogen, preferred reference gas since it is commonly present at such sites;
- of carrying out one or more measurements of the conductivity of the sample(s) of the reference gas and of carrying out the comparison of the measurements obtained with the thermal conductivity values obtained upstream during said "calibration" with this same reference gas;
- of carrying out one or more measurements of the conductivity of the sample(s) of the gas or mixture delivered, and of carrying out the comparison of the measurements thus obtained with the thermal conductivity values obtained upstream during said "calibration"; and
- of giving a diagnosis of "compliant delivery" or "non-compliant delivery" type authorizing or not authorizing the delivery of the gas or mixture delivered.

An example of implementation of the invention is described in detail below.

Consider the case where the deliveries might relate to the following 3 pure gases: nitrogen ($N_2$), oxygen ($O_2$), and carbon dioxide ($CO_2$).

The identification according to the invention is therefore based on the measurement of the thermal conductivity of the gases delivered, which, as is well known in the literature, varies, at a given temperature, significantly for each gas, and hence makes it possible to unambiguously identify the gas present.

The analyzer used was precalibrated with "pure" gases, alone or as mixtures, in various content ranges, for example for $CO_2$—$O_2$ mixtures, and $N_2/O_2$ mixtures.

The device uses two ranges for the measurements: a first range located between $CO_2$ and oxygen, and a second range (for better accuracy) located between nitrogen and oxygen.

The bottom part of the range is calibrated at "0", whilst the top part of the range is calibrated at "$10^6$", in other words each range is calibrated between 0 and 1 million points (ppm).

With a predefined frequency, for example every 3 hours, the device automatically monitors the reference gas in terms of flow rate and identity.

If a variation of conductivity is observed (beyond a certain acceptable deviation set beforehand), the device is automatically recalibrated, whereas if the result lies within the tolerance range, the reference gas is considered to be "recognized" and the equipment is considered to be "ready for operation".

The system uses for example an acceptability criterion of ±10,000 points to identify a gas having the target value of the corresponding range (see example from table 1 below).

TABLE 1

| Gas | Target value | Acceptability criterion |
| --- | --- | --- |
| nitrogen | 0 | −10 000 to +10 000 |
| oxygen | 1 000 000 | 990 000 to 1 010 000 |
| CO2 | 0 | −10 000 to +10 000 |

Once the reference gas has been "monitored", the analysis of at least one sample of gas delivered by the truck to the site is carried out, the example of oxygen (table 1) is taken, here too with an expected target value ($10^6$ ppm), while checking that the result lies within the accepted tolerance range.

If this is indeed the case, the gas is considered to be "recognized" and the delivery is declared to be "compliant", the site delivered to will therefore authorize the transfer of the gas to its storage vessels, whereas if the identification is not compliant, the delivery will be refused.

The identification device is equipped with a configuration profile that comprises in particular the following parameters:
- the gases to be identified (for example $N_2$, $O_2$, $CO_2$).
- the target values in each case and the acceptability criterion (therefore margin).
- the recalibration criterion (therefore the maximum deviation that is authorized).
- the number of test cycles to be carried out (flow rate, pressure, identity).
- the flow rate and pressure ranges.
- the number of purge cycles and the purge time of the sampling line.

A test protocol is consequently set in advance, for example according to the following steps:
- the line for drawing off a gas sample is connected to the device, with for example a pressure of at least 1.5 bar, the measurement operation is started: firstly, the reference gas is monitored (flow rate and identity), if the results lie within the authorized limits it is concluded that the device is operational (qualified) i.e capable of monitoring one or more samples for the identification of the gas delivered;
- the operator is then for example asked to confirm the correct connection of the device with the line for drawing off a gas sample;
- this gas sampling line is then purged, and next the pressure, flow rate and identity of the sampled gas are verified (the number of measurements and the number of values out of scope that are allowed are specified in the configuration profile of the analyzer defined beforehand) and the unit then provides a diagnosis of identity of the gas as "compliant" or "non-compliant", which information can be stored (archived) by the user.

Generally, the activity of the identification device can be archived in a file, in particular to be able to generate, on request of the site to be delivered to, an "identification report".

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of": "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method for on-site monitoring of the quality of a gas delivered to a consumer site, the monitoring being carried out after a delivery of the gas to the consumer site, in order to declare the delivered gases compliant or non-compliant with specifications for the gas, the delivered gas being a single gas or a mixture of gases, said method comprising the steps of:
   providing, after delivery of the gas and receipt thereof at the consumer site, a gas identification device that comprises a thermal conductivity analyzer that has been precalibrated using pure calibration gases or a mixture of pure calibration gases and a data acquisition and processing system;
   acquiring one or more samples of the delivered gas using the gas identification device;
   acquiring one or more samples of a reference gas using the gas identification device;
   carrying out one or more measurements of the thermal conductivity of the sample(s) of the reference gas using the gas identification device;
   using the gas identification device to compare the thermal conductivity measurements of the sample(s) of the reference gas with thermal conductivity values of the pure calibration gas or the mixture of pure calibration gases obtained during said precalibration;
   carrying out one or more measurements of the thermal conductivity of the sample(s) of the delivered gas using the gas identification device;
   using the gas identification device to compare the thermal conductivity measurements of the sample(s) of the delivered gas with the thermal conductivity measurements of the sample(s) of the reference gas; and
   based upon the comparison, by the gas identification device, of the thermal conductivity measurements of the sample(s) of the delivered gas with the thermal conductivity measurements of the sample(s) of the reference gas, using the gas identification device to:
      declare that the delivered gas is compliant with the specifications for the gas and authorize transfer of the delivered gas to storage vessels or,
      declare that the delivered gas is non-compliant with the specifications for the gas and not authorize transfer of the delivered gas to storage vessels.

* * * * *